United States Patent [19]

DiPietropolo

[11] Patent Number: 4,751,922
[45] Date of Patent: Jun. 21, 1988

[54] FLEXIBLE MEDULLARY REAMER

[76] Inventor: Al DiPietropolo, 18 Euclid Ave., Haddonfield, N.J. 08033

[21] Appl. No.: 879,590

[22] Filed: Jun. 27, 1986

[51] Int. Cl.[4] ............................................. A61F 5/04
[52] U.S. Cl. ............................ 128/92 VJ; 128/83; 128/92 VD
[58] Field of Search ........ 128/92 VJ, 92 VV, 92 VD, 128/92 V; 408/127, 199

[56] References Cited

U.S. PATENT DOCUMENTS

| | | | |
|---|---|---|---|
| 2,747,384 | 5/1956 | Beam | 64/2 |
| 3,367,326 | 2/1968 | Frazier | 128/92 VD |
| 3,554,192 | 1/1971 | Isberner | 128/83 |
| 4,541,423 | 9/1985 | Barber | 128/92 E |

FOREIGN PATENT DOCUMENTS

| | | |
|---|---|---|
| 0218492 | 4/1987 | European Pat. Off. . |
| 2542056 | 3/1977 | Fed. Rep. of Germany . |
| 2366826 | 5/1978 | France . |

OTHER PUBLICATIONS

Biomet, Inc., "OEC/Kuntscher Instrumentation", p. G4, 1985.
Richards, "Orthopedic Instruments", p. 208, 1979.
Zimmer Inc., "Updates Section B Trauma Systems", p. S27, 1983.
Synthes, "Instruments for Medullary Reaming", pp. 3-16, date 8/84.

Primary Examiner—Dalton L. Truluck
Assistant Examiner—Colleen Reilly
Attorney, Agent, or Firm—Seidel, Gonda, Goldhammer & Abbott

[57] ABSTRACT

An improved flexible medullary reamer for shaping the medullary space of bones. The shaft is comprised of a single solid element. To permit the use of an elongated guide element, the shaft may be axially bored throughout its length. Attached to the shaft's opposite ends respectively, a cutting head and a means of connecting the shaft to a drive mechanism. To compliment the shaft, said cutting head and connecting means may be centrally bored.

9 Claims, 1 Drawing Sheet

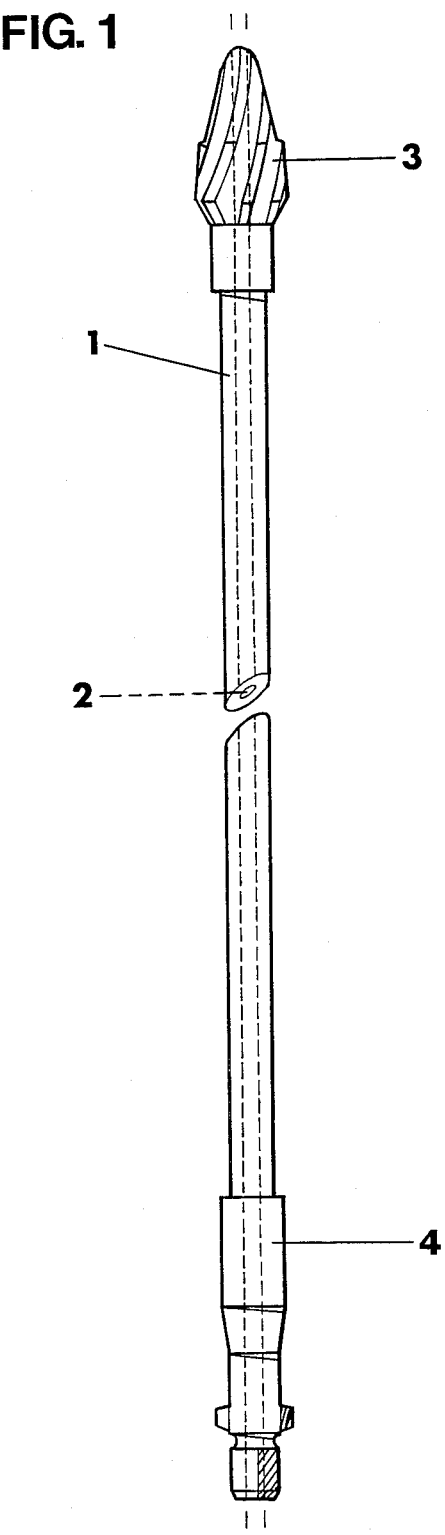
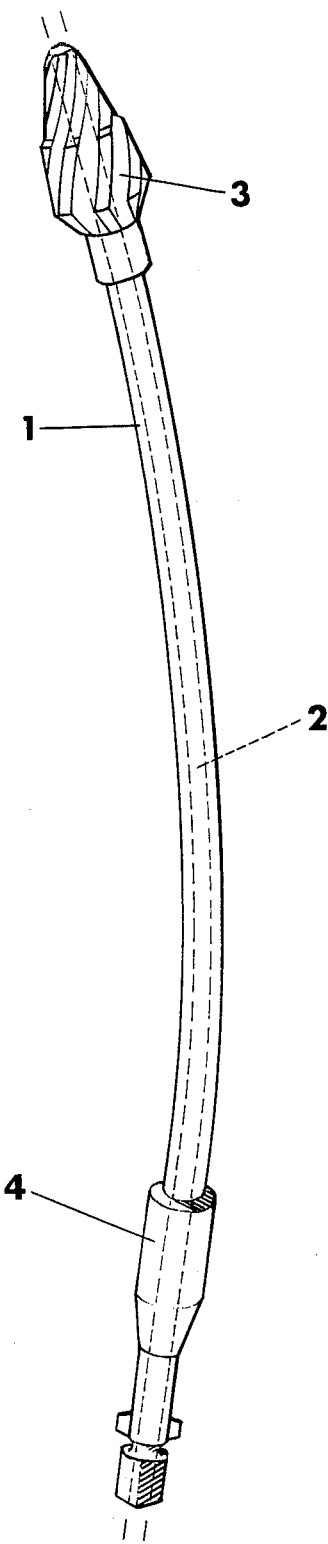

FLEXIBLE MEDULLARY REAMER

FIELD OF THE INVENTION

This invention relates to flexible shafts and specifically to an improved flexible medullary reamer for bones.

BACKGROUND OF THE INVENTION

Medullary canal reamers of this type are used to enlarge the medullary canals of bone in preparation for the insertion of fixation devices, performing an intramedullary osteotomy, stimulating bone growth, the insertion of a plug to preclude bone cement from migrating while it is in its viscous state, and for other reasons. The medullary canals of bone are seldom straight. More typically the canal will have some degree of curvature to it. Should a straight and rigid series of reamers be employed to enlarge the canal there is considerable likelihood that the reamer, in not being capable of following the bone's curvature, will not remove the desired uniform amount of bone tissue. In such a situation, excessive tissue removal occurring in at least one plane will be experienced as the reamer is advanced. For this reason medullary canals are almost always prepared with reamers having a flexible shaft.

Heretofore, flexible medullary reamers are of two types. The first to come into common usage consisted of spiral or helically wound metal wire(s) or strip(s), which comprised the shaft of the reamer. A disadvantage of this design is that these reamers can be operated only in the forward mode of rotation. If operated in the reverse mode, which occasionally is required to free a lodged reamer and to facilitate normal removal, the shaft unwinds, thus rendering the reamer permanently deformed, unusable, and unrepairable. This adds considerably to the cost of maintaining a serviceable set of medullary reamers. Further, a lodged cutting head may subsequently be extremely difficult, if not impossible to remove without further violation of the involved bone and surrounding tissues. Another disadvantage of said design is the extreme difficulty in their proper and thorough cleaning after use. The spiral or helically wound metal shafts contain many voids of various sizes. Blood and tissue readily infiltrate such voids and become trapped within the confines of the shaft. When the reamer is in use the voids are considerably distorted and enlarged as the reamer is advanced towards and within the medullary canal, thus providing ready access for the particles of tissue. Prior to use, all medullary reamers are sterilized and hopefully, the blood and tissue particles not evacuated during the cleaning process and remaining within the interstices of the reamers, are at least rendered harmless. However, depending upon the amount and composition of the extraneous particles and their degree of isolation from the sterilizing process, said particles may not be rendered sterile. Even in a sterile condition these foreign particles may still cause problems of infection should they become dislodged from the confines of the reamer and come into contact with the patient's internal tissues. Medical professionals recognize this problem but acquiesce to using these reamers for lack of an acceptable alternative. A further disadvantage of this medullary reamer is that the torsional load it is subject to when in use results in poor power transfer and varying degrees of distortion of said shaft. If the power source providing the rotational energy to the reamer is great enough, said coils may tighten sufficiently to adversely affect the intended flexibility of the shaft. Another disadvantage associated with a psiral or helically wound reamer is the trauma it imposes to surrounding tissues. This results when the shaft of the reamer is not completely within the medullary canal as would occur during the initial reaming process. As the shaft rotates, that portion remaining outside of the medullary canal can become excessively flexed and distorted, thus enlarging the voids between the coils of the shaft. As the flexed shaft rotates, tissue lying outside of the canal and unintended for removal, becomes trapped within the voids and are torn from their underlying structures.

A second distinct type of flexible medullary reamer is described in the literature. The shaft of the reamer embodies a plurality of parallel, flexible elements joined together at opposite ends by means of a welded or soldered connection. A disadvantage of this shaft is that proper cleaning is difficult to accomplish. Towards its opposite ends where the individual elements converge, said elements come in close contact with each other until the final termination point is reached where they are permanently welded or soldered together to form a solid mass. Where these elements begin to converge, blood and tissue can readily become trapped and prove difficult to remove during the cleaning process. Another disadvantage of this flexible reamer is the excessive noise generated in its use which is caused by the individual elements being twisted and forcefully whipped into contact with each other. A further disadvantage of said flexible reamer occurs during usage. As rotation occurs, the individual elements spirally tighten around each other causing the shaft to become more rigid and thereby reducing the shaft's flexibility and increasing the likelihood of the attached cutting head not properly adhering to the central path of the medullary canal. Another disadvantage of said flexible reamer is the shaft's tendency, as it rotates but not yet fully within the confines of the medullary canal, to tear tissue from underlying structures as the individual elements are torsionally loaded and unloaded, thereby enlarging and contracting the spaces between the individual elements sufficiently to trap uninvolved tissue between the individual wires and tearing them free. Another disadvantage of said flexible reamer occurs in attempting to utilize the central bore of the reamer. The central bore is intended to receive a long small diameter guide pin which had previously been inserted into the medullary canal to act as a track for the advancing reamer. Except at its respective ends, this reamer lacks a well-defined and bordered central bore. Therefore, it is difficult to prevent the guide pin from exiting the reamer in the area of the free standing wires during the initial positioning of the guide pin within the reamer. A further disadvantage of this flexible shaft is the inefficient transfer of energy from the power source to the cutting head which is caused by the twisting and wrapping together of the individual elements as the reamer is rotated.

OBJECTS OF THE INVENTION

Accordingly the objects of my invention are to provide a medullary reamer which is more appropriate to surgical use in that it can be easily cleaned, thus assuring a sterile and biologically safe instrument when properly autoclaved. Other objects include the reduction of trauma to extraneous tissue, a more easily used instrument, one that is more efficient in transferring power from the energy source, more durable than existing reamers, less expensive to manufacture, operable in the reverse mode of rotation, and retaining the required degree of flexibility under maximum load.

These and other objects of the present invention will become apparent from the following and claims in conjunction with the drawing. Variations and modifications may be made within the scope of the claims and portions of the improvements may be used without others.

SUMMARY OF THE INVENTION

In applying the improvement under the invention to the already known method of manufacturing flexible medullary reamers, the principle continues to be utilized that a flexible shaft with a cutting head at one end and at its opposite end a means of attaching said reamer to a rotational drive mechanism for the purpose of modifying medullary canals of bone.

Flexible medullary reamers provided with the improved shaft according to the invention, maintain the basic ability of enabling the attached cutting head to follow the curvature of the bone in an unimpeded manner as it is advanced within the medullary canal, and remaining unaffected by the inevitable mal-alignment of the reamer shaft. To achieve this and eliminate the many shortcomings of existing reamers, the improvement provides for the utilization of a shaft comprised of a monolithic etement. The selected material must possess the required degree of flexibility, torsional strength, resistance to abrasion and the ability to be repeatedly steam sterilized. Said shaft may contain a central longitudinal bore for the purpose of receiving an elongated guide pin previously positioned within the bone's medullary space.

The improved shaft, in either aforementioned configuration, eliminates the voids and interstices where tissue may become trapped and hidden from view, thereby providing a more appropriate instrument for surgical procedures. Although unremoved particles may be sterilized during the autoclaving process, their subsequent dislodgement within an ensuing patient may prove to be quite detrimental. Infections within the bone are of a most serious nature and extremely difficult and expensive to treat. The improved shaft in having a solid and continuous surface is quickly and easily cleaned. The well-defined central bore is readily cleansed by passing a bristle brush throughout its length. A visual examination will quickly verify the cleanliness of the reamer. Thus, subsequent sterilization is assured when properly performed. The smooth outer surface of the improved shaft will minimize the trauma and disruption of surrounding tissues as the reamers are used.

The improved shaft maintains its original flexibility under torsional loading and does not in itself create any noise when used. Power transfer from the drive mechanism to the cutting head is very efficient with the improvement.

Due to its smooth inner bore, the improvement facilitates the insertion of the generally used guide pin within the bore of the reamer. This expedites operative time which is significant to the well-being of the involved patient and helps contain the financial charges to the patient.

This improved shaft also permits the reamer to be operated in the reverse mode of rotation with optimal efficiency and no adverse effects. Occasionally, a reamer will become firmly lodged within the medullary space. Forward rotation seldom frees the reamer and extensive extractive efforts must be employed to remove the offending device. With a reversible reamer, a lodged cutting head is quickly removed.

Manufacturing and labor costs associated with the improved shaft are less due to the fewer parts, ease of assembly and a lower unit cost of the shaft. The improved shaft is easy to use and not prone to becoming damaged or abused. Consequently, replacement reamers will seldom need to be purchased, thus increasing the cost effectiveness of the reamer.

BRIEF DESCRIPTION OF THE DRAWING

Said drawings show in the following figures:

FIG. 1 is a side, partial cross-sectional view of a flexible medullary reamer.

FIG. 2 is a view of the flexible medullary reamer in a deflected position.

DETAILED DESCRIPTION OF THE PREFERRED EMBODIMENT

Referring to FIGS. 1 and 2, the shaft 1 in its preferred embodiment is comprised of a flexible elongated cylindrical body which may be centrally bored in the longitudinal axis to receive an elongated guide pin (not shown). The diameter and length of said shaft may be varied to meet specific requirements. A typical embodiment utilizing a 13 millimeter cutting head will have a shaft seven millimeters in diameter and be twenty inches in length. The outer diameter of the cutting head should be greater than the shaft diameter. If centrally bored to receive a guide pin, a typical bore diameter will be 0.144 which will be sufficient to accept the frequently used one-eighth inch diameter guide pin.

Cutting head 3 is attached to shaft 1 by means of a suitable bonding agent or other method as known to those skilled in the art. Generally, cutting heads for medullary reamers are produced from stainless steel or tungsten carbide. The cutting head 3 may have a central channel to receive a guide pin. The cutting head may be secured to the shaft by adhesive bonding, by heating the end of the shaft sufficiently to permit the shaft material to become softened and directed to flow into the inner spaces of the metal cutting head, by incorporating the connector end of the cutting head into the flexible shaft during the manufacturing of the shaft by embedding said connector end into the shaft material by means of extending the filaments and resin which comprise the shaft to include said connector end, by mechanical means or a combination of the aforementioned methods. An alternative embodiment would utilize removeable cutting heads which are mechanically attached to a suitable adaptor connected to the flexible shaft by any of the methods previously described. The diameter and configuration of said cutting head may vary from 3.

Adaptor 4 is a separate body, usually of stainless steel attached to 1 by the methods previously described for the attachment of the cutting heads. The function of 4 is to be the means of connecting the reamer to a complimentary drive mechanism of the power source. It follows that the requirements of the driving mechanism will dictate the configuration of 4. Adaptor 4 may be centrally bored to receive a guide pin. However, it will generally be found that an adaptor will minimize wear and damage to the end shaft of the reamer and also be of great convenience in permitting a quick and positive means of securing the reamer to the drive mechanism.

Adaptor 4, if used, may be secured to shaft 1 by the aforementioned methods of attaching the cutting heads.

Although the preferred embodiment of the present invention has been described in detail, it is contemplated that modifications may be made all in accordance with the spirit and scope of the present invention.

What is claimed is:

1. In a flexible medullary rotational reamer for clearing, enlarging or otherwise modifying the medullary space of bones, having a flexible shaft with a cutting head at one end and an adaptor piece at its opposite end for connecting said shaft to a rotational drive element thereby causing rotation of the shaft, said shaft having a small diameter axial bore throughout its length to receive an elongated guide element, the improvement comprising:
   said flexible shaft being comprised of a material from the group consisting of carbon fiber composites.

2. In a flexible medullary rotational reamer for clearing, enlarging or otherwise modifying the medullary space of bones, having a flexible shaft with a cutting head at one end and an adaptor piece at its opposite end for connecting said shaft to a rotational drive element thereby causing rotation of the shaft, said shaft being comprised of a material from the group consisting of thermoplastics and composites thereof.

3. The flexible medullary rotational reamer of claim 1 wherein said shaft is formed by extrusion, pultrusion, molding, laminating, machining or bonding.

4. The flexible medullary rotational reamer of claim 1 wherein at least one of said adaptor and cutting head is secured to said shaft.

5. A flexible medullary rotational reamer for clearing, enlarging or otherwise modifying the medullary space of bones, comprising:
   a flexible monolithic shaft comprised of a material from the group consisting of fiber reinforced composites,
   said shaft with a rotational cutting head at one end thereof and a rotational drive coupling at an opposite end thereof,
   said shaft having an axial bore for accepting a guide element.

6. A flexible medullary rotational reamer for clearing, enlarging or otherwise modifying the medullary space of bones, comprising:
   a flexible monolithic shaft comprised of a synthetic plastic material,
   said shaft with a rotational cutting head at one end thereof and a rotational drive coupling at an opposite end thereof,
   said shaft having an axial bore for accepting a guide element.

7. The flexible medullary rotational reamer of claim 5 or claim 6 wherein said shaft is comprised of a material from the group consisting of thermoplastics and thermosets.

8. The flexible medullary rotational reamer of claim 5 or claim 6 wherein said shaft has an axial bore for accepting a guide element.

9. The flexible medullary rotational reamer of claim 5 or claim 6 wherein said shaft is formed by extrusion, pultrusion, molding, laminating, wrapping, braiding, machining or bonding.

* * * * *